United States Patent [19]

Rasmussen

[11] 4,379,786

[45] Apr. 12, 1983

[54] N-ARYL-N-(4,5,6,7-TETRAHYDRO-1H-1,3, DIAZEPIN-2-YL)UREAS AS ANTIHYPERTENSIVES

[75] Inventor: Chris R. Rasmussen, Ambler, Pa.

[73] Assignee: McNeilab, Inc., Fort Washington, Pa.

[21] Appl. No.: 306,270

[22] Filed: Sep. 28, 1981

Related U.S. Application Data

[62] Division of Ser. No. 159,987, Jun. 16, 1980, abandoned.

[51] Int. Cl.$^3$ .............................................. A61K 31/55
[52] U.S. Cl. .............................. 424/244; 260/239 BC
[58] Field of Search ......................................... 424/244

[56] References Cited

U.S. PATENT DOCUMENTS 3,168,520  2/1965  Kleeman et al. ..................... 544/332

OTHER PUBLICATIONS

Douglas, G., et al., *Arzneim–Forsch.*, 28, 1435–1441 (1978).

*Primary Examiner*—Richard A. Schwartz

[57] ABSTRACT

N-(Substituted phenyl)-N'-(4,5,6,7-tetrahydro-1H-1,3-diazepin-2-yl)ureas, and pharmaceutically-acceptable salts thereof, are disclosed, as are compositions containing said ureas in a pharmaceutically-acceptable carrier, to have antihypertensive activity and to be useful in a method of reducing arterial pressure in hypertensive subjects.

6 Claims, No Drawings

N-ARYL-N-(4,5,6,7-TETRAHYDRO-1H-1,3, DIAZEPIN-2-YL)UREAS AS ANTIHYPERTENSIVES

This is a division of application Ser. No. 159,987, filed June 16, 1980, now abandoned.

FIELD OF INVENTION

This invention relates to a method for controlling hypertension employing certain N-aryl-N'-(4,5,6,7-tetrahydro-1H-1,3-diazepin-2-yl)ureas, to said urea compounds per se, and to pharmaceutical compositions containing said urea compounds.

BRIEF SUMMARY OF THE INVENTION

The present invention involves a method of reducing arterial pressure in hypertensive animals by administering to a hypotensive subject, in a pharmaceutically-acceptable carrier, a therapeutically-effective amount of a compound, or a pharmaceutically-acceptable salt thereof, having the formula:

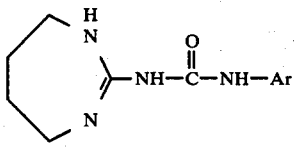

(I)

or a pharmaceutically-acceptable acid addition salt thereof. It also embraces compositions suitable for such application wherein the foregoing urea compound is in admixture with a pharmaceutically-acceptable carrier. It further embraces the foregoing urea compounds per se.

In the foregoing and subsequent formulas, Ar is phenyl substituted with from 1-3 substituents chosen from halo (F, Cl and Br), $CH_3$, $CF_3$, and $OCH_3$. In the more preferred compounds of the inventions, Ar may be represented by

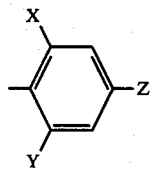

wherein X=Br, Cl, F, $CH_3$, $CF_3$, or $OCH_3$; Y=H, Cl, Br, $CF_3$, F, $CH_3$, or $OCH_3$; and Z=H or F. In the most preferred compounds of the inventions: X is Br, Cl, $CH_3$ or $CF_3$; Y is H, Cl, Br, $CH_3$, or $CF_3$; and Z is H.

The activities of the above compounds residue in the urea base so that useful acid addition salts may be from various acids provided only that the acids be pharmaceutically-acceptable. Representative acid salts include hydrochloride, hydrobromide, phosphate, sulfate, p-toluenesulfonate, benzenesulfonate, malonate, succinate, methosulfate, methanesulfonate, 2-napsylate and the like.

PRIOR ART

An article by G. H. Douglas, et al., *Arzneimittel Forschung.*, Vol. 28 (II) Supplement 8a, 1435–1441 (1978) erroneously discloses as Compound 110 at p. 1438 (in its tautomeric form) the compound of the formula:

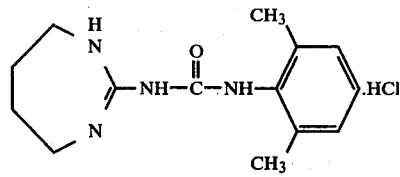

which was disclosed to be active as a gastric acid antisecretory agent. The article does not teach the antihypertensive activity for this 2,6-dimethylphenyl compound, which applicant found to exist.

The columns headed by $R^2$ and $R^3$ in Table 3 on p. 1438 of the article were transposed erroneously leading to the above structure, which was then disclosed in *Chem. Abstracts*, 90, 48236s (1979), where it was named in the *Chem. Abstracts*, Vol. 90, 1979—Formula Index and given a Chem. Abstracts Registry Number.

METHOD OF PREPARATION

The pharmacologically useful N-aryl-N'-(4,5,6,7-tetrahydro-1H-1,3-diazepin-2-yl)urea compounds are prepared from 2-amino-4,5,6,7-tetrahydro-1H-1,3-diazepine, which has the structure:

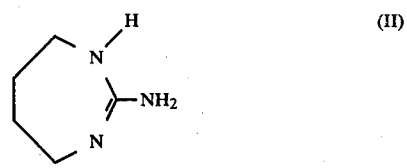

(II)

and which is a known compound, and is prepared as follows:

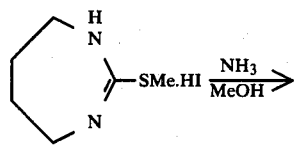

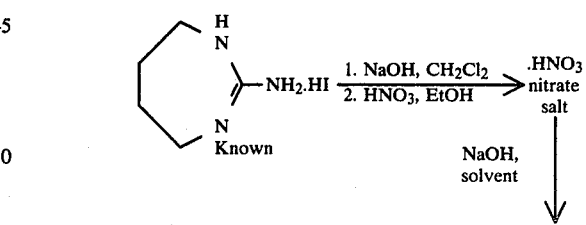

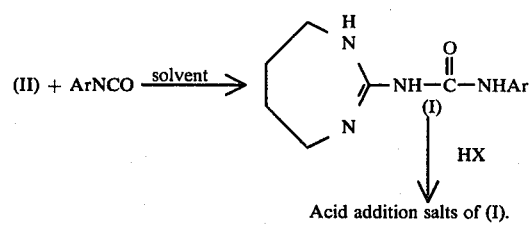

Acid addition salts of (I).

The free base form of II can be generated by treating a stirring suspension of II .HI or $HNO_3$ in solvents such as $CH_2Cl_2$ (methylene chloride), tetrahydrofuran, dioxane, and the like with strong bases such as aqueous NaOH (50%), concentrated KOH, and the like; NaOH (50%) being preferred. The resulting solution of free base II is dried over a suitable drying agent such as $Na_2SO_4$ $K_2CO_3$. The dried solutions may either be used as reactions with aryl isocyanates to obtain products I or the extraction solvent may be evaporated in vacuo and the residual free base II taken up in a different organic solvent, e.g., DMF, DMSO, and the like; said solutions of II then being treated with an appropriate isocyanate III to afford the free base products I. Although the reactions of II with III may be carried out with equimolar amounts of reactants, usually a stoichiometric excess, generally of from about 0.25–1.0 mole of free base II to that of aryl isocyanate III is employed in order to minimize undesired side reactions such as, for example, formation of bis-aryl isocyanate adducts with II. Temperature ranges for those reactions may conveniently range from about −20° to 70° C. The products I, obtained in free base form, may conveniently be purified by dissolving in an organic solvent, immiscible with $H_2O$, such as $CH_2Cl_2$, washing with $H_2O$ to remove excess II, if any, followed by isolation of I from the solvent by drying, filtration from drying agent, and solvent removal.

Alternatively, the reactions of II free base with III may be carried out by adding a solution of II HCl in DMF, DMSO, and the like, to a stirring suspension of a stoichiometric amount of an alkali metal hydride such as LiH, NaH, and the like, LiH being preferred, which forms II free base, the corresponding alkali metal chloride, and $H_2$ gas.

The thus obtained solution of free base II (the presence of the metal chloride does not interfere with the subsequent reaction) is treated with an appropriate amount of aryl isocyanate III. When the reaction is complete, dilution with $H_2O$ or ice-$H_2O$, in excess amounts, causes precipitation of crude product I and leaves any unreacted II in solution. Filtration then allows isolation of crude I.

Said I, in free base form, may be further purified, if necessary, by recrystallization and chromatographic techniques, and so forth, according to standard techniques known in the art. A further purification method may be used such as dissolution in dilute aqueous acid, such as HCl, most preferred, $H_2SO_4$, HBr, $HNO_3$ and the like, filtration from any undissolved impurities, followed by neutralization with suitable inorganic bases such as sodium and potassium bicarbonates and carbonates and the like, dilute alkali metal hydroxides such as NaOH, KOH, and the like, and organic bases such as triethylamine, diisopropylethylamine, and the like, which causes precipitation of I free base. The thus-obtained free base I may then be purified by recrystallization, etc., as described above, or may be converted to a suitable pharmaceutically-acceptable salt form of I which also may be purified by recrystallization or precipitation techniques well known in the art.

Said pharmaceutically-acceptable salt forms of I are generally comprised of I in combination with suitable mineral acids such as HCl (most preferred), HBr, $H_2SO_4$, $H_3PO_4$, and strong organic acids such as benzenesulfonic, p-toluenesulfonic, 1- and 2-naphthalenesulfonic, ethanedisulfonic, methane- and ethanesulfonic methylsulfuric, and the like, being the most preferred. Although salts of I with weaker acids, such as benzoic, fumaric, maleic, citric, etc. do form, they are relatively easily dissociated because of the relatively weak base strength of I. This dissociation may be caused by attempted drying in vacuo, dissolution in $H_2O$, etc. The ease of dissociation, however, may not necessarily preclude use of salts of this type in pharmaceutical formulations insofar as they remain stable enough to be purified by recrystallization, etc., and capable of being formulated into pharmaceutical preparations such as tablets, capsules, and the like.

The preferred salt forms of I are additionally capable of forming hydrates and solvates with $H_2O$ and certain organic solvents, respectively. Also, I and its salt forms may exist in several tautomeric forms. It is naturally intended that the various hydrates, solvates, and tautomeric forms of I be included within the scope of this invention.

The N-(substituted phenyl)-N'-(4,5,6,7-tetrahydro-1H-1,3-diazepin-2-yl)urea compounds useful in the present invention have been found to alleviate hypertension and further, to generally accomplish this without an accompanying increase in heart rate. The compounds most useful in the present invention do not show an increase in heart rate, but a lowering of heart rate and, generally, long duration. An agent which has an antihypertensive effect without increasing but rather maintaining or decreasing heart rate, is the one considered most useful for beneficially treating a hypertensive subject. The extent to which a compound possesses these properties may be primarily determined in the antihypertensive test hereinafter described.

Rodent Antihypertensive Screen

This test evaluates compounds for effects on arterial pressure and heart rate. In this test, the arterial pressure of adult spontaneously hypertensive rats [SHR] (Charles River) is monitored directly via an aortic cannula. The SHR rats are anesthetized with an inhalation anesthetic (methoxyflurane). The left carotid artery is isolated and cannulated. The tip of the cannula is advanced to the aorta and the cannula is exteriorized behind the neck at the level of the scapula. Animals are placed in individual cases and allowed to recover from the anesthetic and are kept unrestrained. The arterial cannula is connected to the pressure transducer which is attached to the recorder. Heart rate is determined from the arterial pressure recording. The test compounds are administered either orally (p.o.) by gavage or by intraperitoneal (i.p.) injection. The arterial pressure and heart rate are monitored for a minimum of 24 hours. A test compound is considered to be active as an antihypertensive agent if the mean arterial pressure (MAP) indicates a fall of >15 mm of Hg. Each animal serves as his own control.

The results of this test employing at least 3 rats per dose level for each compound and performed with N-aryl-N'-(4,5,6,7-tetrahydro-1H-1,3-diazepin-2-yl)urea compounds are shown in Table I.

The results seen in Table I show that N-(substituted phenyl)-N'-(4,5,6,7-tetrahydro-1H-1,3-diazepin-2-yl)urea compounds and their salts possess not only the beneficial antihypertensive property but also the desirable property of maintaining or lowering heart rate.

The compounds of the present invention are useful for treating hypertension (high blood pressure) by administering to subjects in need of treatment, a therapeutically-effective hypertension reducing amount of a N-(substituted phenyl)-N'-(4,5,6,7-tetrahydro-1H-1,3-diazepin-2-yl)urea compound of Formula I or its pharmaceutically-acceptable salt as active agent. The active agents may be administered with or without carrier in the amounts hereinafter set forth. A preferred method of administration is by the use of pharmaceutical compositions in unit dosage form as described below.

The operable ranges for carrying out the treatment is the administration, orally or parenterally, of from about 1 milligram to about 500 milligrams of said N-(substituted phenyl)-N'-(4,5,6,7-tetrahydro-1H-1,3-diazepin-2-yl)urea compound in dosage unit form. While the therapeutic method is most useful for human subjects, it may also be employed for other mammals. Operable amounts are generally within the range of from about 0.5 to 100 mg/kg of body weight.

duce the desired therapeutic effect in association with the required pharmaceutical carrier. Examples of such dosage unit forms are tablets, capsules, pills, powder packets, wafers, teaspoonful, tablespoonful and the like, and segregated multiples thereof. A dosage unit generally will contain from about 1 to about 500 mg of the N-(substituted phenyl)-N'-(4,5,6,7-tetrahydro-1H-1,3-diazepin-2-yl)urea compound.

The following examples illustrate the preparation of the N-(substituted phenyl)-N'-(4,5,6,7-tetrahydro-1H-1,3-diazepin-2-yl)urea compounds and the novel pharmaceutical compositions suitable in the practice of the

TABLE I
ANTIHYPERTENSIVE AND CARDIAC RATE DETERMINATIONS

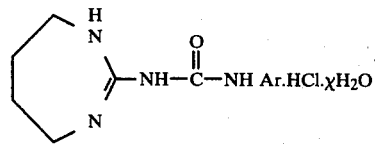
NH—C(=O)—NH Ar.HCl.χH$_2$O

| | | | SHR Rat | | |
| --- | --- | --- | --- | --- | --- |
| Ar | χ | McN— | ΔMAP in. mm Hg (mg/kg, route) | ΔHR in beats/min. | Duration in Hours |
| 2,6-Cl$_2$Ph | 0.5 | 4967-11-98 | −49(35 p.o.) | −78 | 21 |
| | | | −50(30 p.o.) | −124 | >24 |
| | | | −48(10 p.o.) | −67 | 23 |
| | | | −31(1 p.o.) | −64 | 17 |
| 2-CF$_3$Ph | 0 | 5036-11 | −43(30 i.p.) | +39 | <1 |
| | | | −39(100 p.o.) | −98 | 11 |
| 2,6-Me$_2$Ph | ⅛ | 5076-11-98 | −94(30 i.p.) | −127 | >24 |
| | | | −64(100 p.o.) | −112 | >24 |
| 2-Cl—6-MePh | ⅛ | 5075-11-98 | −81(30 i.p.) | −108 | 17 |
| | | | −58(100 p.o.) | −104 | 23 |
| 2,6-Br$_2$—4-F Ph | 0 | 5037-11 | −30(30 i.p.) | +58 | 1 |
| | | | −43(100 p.o.) | +41 | 23 |
| 2,6-(OMe)$_2$Ph | 0 | 5040-11 | −87(30 i.p.) | +62 | 1 |
| | | | −79(100 p.o.) | −50 | 11 |

MAP = Mean arterial pressure
Δ = Change
HR = Heart Rate

Pharmaceutical compositions containing the N-(substituted phenyl)-N'-(4,5,6,7-tetrahydro-1H-1,3-diazepin-2-yl)urea compounds of the present invention or acid addition salt thereof, as the active ingredient, may be prepared by intimately mixing the urea compound with a pharmaceutical carrier according to conventional pharmaceutical compounding techniques, which carrier may take a wide variety of forms depending on the form of preparation desired for administration, e.g., oral or parenteral. In preparing the compositions in oral dosage form, any of the usual pharmaceutical media may be employed, including liquid carriers such as water, glycols, oils, alcohols and the like for oral liquid preparations such as suspensions, elixers and solutions; and solid carriers such as starches, sugars, kaolin, calcium stearate, ethyl cellulose, etc., including materials which function as lubricants, binders, disintegrating agents and the like for powders, capsules and tablets. Because of their ease in administration, tablets and capsules represent the most advantageous oral dosage form. These compositions employ solid pharmaceutical carriers such as the aforementioned starches, sugars, kaolin and the like, generally with a lubricant such as calcium stearate. It is especially advantageous to formulate the aforementioned pharmaceutical compositions in dosage unit form for ease of administration and uniformity of dosage. The term "dosage unit form" as used in the specification and claims herein refers to physically discrete units suitable as unitary dosages, each unit containing a predetermined quantity of active ingredient calculated to proinvention but are not to be construed as limiting:

EXAMPLE IA

2-Amino-4,5,6,7-tetrahydro-1H-1,3-diazepine Mononitrate

A suspension of 217.9 g 2-(methylthio)-4,5,6,7-tetrahydro-1H-1,3-diazepine hydroiodide in 400 ml of MeOH was treated with anhydrous NH$_3$ (NaOH traps+NaCl traps) vigorously for 1 hour. All the solid dissolved. The solution was saturated with NH$_3$ and let stand over the weekend at room temperature. TLC showed the reaction to be essentially complete. The MeOH was boiled off replacing with t-BuOH then cooled and Et$_2$O added gave the HI salt (hygroscopic). The material was converted to the free base in CH$_2$Cl$_2$. The organic layer was dried (K$_2$CO$_3$), filtered and the solvent removed in vacuo affording a heavy oil. The oil was taken up in absolute EtOH and carefully neutralized with HNO$_3$ (conc. aqueous). A little solid impurity precipitated, early on, which should have been removed and discarded. Before the acid had all been added, the mixture became too thick to mix thoroughly. A first crop of the salt was collected and washed with fresh EtOH (95%). The filtrate was then neutralized to pH 7 affording a second crop. Recrystallization of these crops was a long and tedious process using MeOH-EtOH (95%) then boiling off the MeOH and filtering hot from less soluble inorganic impurities. After many recrystallizations, a crop of quite pure product was obtained, 24.7 g (12.8%); m.p. 165°–167° C., less pure crop; m.p. 156°–161.5° C., 20.9 g (10.8%); IR (KBr) 3251, 3108, 1660, 1598 cm$^{-1}$.

ANAL. Calcd. for $C_5H_{11}N_3 \cdot HNO_3$ (113.16/176.175): C, 34.09; H, 6.87; N, 31.80. FOUND: C, 34.28; H, 6.36; N, 31.59.

EXAMPLE 1B

N-(2,6-Dichlorophenyl)-N'-(4,5,6,7-tetrahydro-1H-1,3-diazepin-2-yl)urea Monohydrochloride Hemihydrate A 300-ml flask was charged with 12.1 g (0.05 mol) of 2-amino-4,5,6,7-tetrahydro-1H-1,3-diazepine hydroiodide 1), 10.0 g of 50% NaOH and 70 ml of THF. After stirring at room temperature for 1 hour, 10.0 g $Na_2SO_4$ was added and the mixture was stirred for an additional 1.5 hours. The reaction mixture was cooled to $-30°$ C. (2-PrOH, dry ice) and a solution of 6.3 g (0.033 mol) of 2,6-dichlorophenyl isocyanate in 80 ml of THF was added over a period of 2 hours. At the end of addition, the reaction mixture was allowed to warm to room temperature and stirring continued for 1 hour. The solids, were filtered and the filtrate evaporated in vacuo. The residue was dissolved in dilute HCl, insolubles removed by filtration, and the aqueous solution washed with ether, made basic with cold 30% NaOH, and extracted with $CH_2Cl_2$. The combined organic layers were dried ($K_2CO_3$), filtered through a pad of diatomaceous earth and evaporated in vacuo. The residue was dissolved in MeOH, neutralized with ethereal HCl and treated with ether to give crystals which were recrystallized from MeOH/ether and then from a minimum amount of $H_2O$ to give pure N-(2,6-dichlorophenyl)-N'-(4,5,6,7-tetrahydro-1H-1,3-diazepin-2-yl)urea monohydrochloride hemihydrate; m.p. (175) 177°–179° C. dec. UV max. (MeOH) 244 ($\epsilon$20,100) and 224 nm shld ($\epsilon$20,800); IR (KBr) 3420, 3200, 1710, 1675, 1535 cm$^{-1}$.

ANAL. Calcd. for $C_{11}H_{14}Cl_2N_4O \cdot HCl \cdot 0.5H_2O$: C, 41.59; H, 4.65; N, 16,16; $H_2O$, 2.60. FOUND: C, 41.88; H, 4.70; N, 16.12; $H_2O$, 2.92.

(1) P. Stefanye, William L. Howard, *J. Am. Chem. Soc.*, 77, 761(1955) and Brit. Pat. No. 612,693, Nov. 16, 1948; *Chem. Abstr.*, 43, 6670d (1949). Material dried in vacuo at 50° C. (5 mm Hg) 4 hours (to constant weight).

EXAMPLE 11

N-(4,5,6,7-tetrahydro-1H-1,3-diazepin-2-yl)-N'-(2-trifluoromethylphenyl)urea Monohydrochloride A mixture of 7.40 g (0.042 mol) of 2-amino-4,5,6,7-tetrahydro-1H-1,3-diazepine mononitrate, 10 g (0.12 mol) of 50% NaOH and 75 ml of THF was stirred at room temperature for 1 hour and then 10 g $Na_2SO_4$ was added. After stirring for 1 hour, a solution of 6.55 g (0.035 mol) of 2-trifluoromethylphenyl isocyanate in 60 ml of THF was added over a period of 1 hour and stirring continued for 1 hour. The reaction mixture was filtered, the filtrate evaporated in vacuo and the residue dissolved in 20 ml of 10% HCl and 30 ml of $H_2O$ with warming. After filtration through a pad of diatomaceous earth, chilling in ice gave the crystalline hydrochloride which was recrystallized from MeOH/ether. Drying in vacuo (20° C., 5 mm Hg) to constant weight afforded 8.13 g (69%) of the pure N-(4,5,6,7-tetrahydro-1H-1,3-diazepin-2-yl)-N'-(2-trifluoromethylphenyl)urea monohydrochloride, m.p. (185) 190°–192° C.; IR (CHCl$_3$) 3208, 1716, 1671, 1643 cm$^{-1}$. UV max. (MeOH) 280 infl. ($\epsilon$7,100), 258 ($\epsilon$19,100) and 219 nm infl. ($\epsilon$11,600).

ANAL. Calcd. for $C_{13}H_{15}F_3N_4O \cdot HCl$: C, 46.37; H, 4.79; N, 16.64. FOUND: C, 46,37; H, 4.83; N, 16.61.

EXAMPLE III

N-(2,6-Dibromo-4-fluorophenyl)-N'-(4,5,6,7-tetrahydro-1H-1,3-diazepin-2-yl)urea Monohydrochloride A mixture of 5.30 g (0.030 mol) of 2-amino-4,5,6,7-tetrahydro-1H-1,3-diazepine mononitrate, 10.0 g (0.12 mol) of 50% NaOH and 100 ml of THF was stirred at room temperature for 1 hour and then 10 g $Na_2SO_4$ was added. After stirring for 1 hour a solution of 7.37 g (0.025 mol) of 2,6-dibromo-4-fluorophenyl isocyanate in 50 ml of THF was added over a period of 1 hour and stirring continued for 1 hour. The reaction mixture was filtered, the filtrate evaporated in vacuo and the residue dissolved in 15 ml of 10% HCl and 130 ml of $H_2O$ with warming. After filtration through a pad of diatomaceous earth, chilling in ice gave the crystalline hydrochloride which was recrystallized from MeOH/ether. Drying to constant weight in vacuo (20° C., 5 mm Hg) afforded 5.45 g (50%) of pure N-(2,6-dibromo-4-fluorophenyl)-N'-(4,5,6,7-tetrahydro-1H-1,3-diazepin-2-yl)urea monohydrochloride; m.p. (175) 183°–185° C. dec.; IR (CHCl$_3$) 3161, 1716, 1669, 1641 cm$^{-1}$. UV max. (MeOH) 238 ($\epsilon$23,000) and 227 nm infl. ($\epsilon$21,800).

ANAL. Calcd. for $C_{12}H_{13}Br_2FN_4O \cdot HCl$: C, 32.42; H, 3.17; N, 12.60. FOUND: C, 32.15; H, 2.97; N, 12.41.

EXAMPLE IV

N-(2,6-Dimethoxyphenyl)-N'-(4,5,6,7-tetrahydro-1H-1,3-diazepin-2-yl)urea Monohydrochloride A mixture of 7.40 g (0.042 mol) of 2-amino-4,5,6,7-tetrahydro-1H-1,3-diazepine mononitrate, 15 g (0.20 mol) of 50% NaOH and 100 ml of THF was stirred at room temperature for 1 hour and then 10 g $Na_2SO_4$ was added. After stirring for 1 hour, a solution of 6.30 g (0.035 mol) of 2,6-dimethoxyphenol isocyanate in 50 ml of THF was added over a period of 1 hour and stirring continued for 1 hour. The reaction mixture was filtered, the filtrate evaporated in vacuo and the residue dissolved in 12 ml of 10% HCl and 50 ml of $H_2O$ with warming. After filtering through a pad of diatomaceous earth, the solution was chilled and washed with 2×50 ml of ether. The aqueous layer was made basic with cold 20% NaOH and extracted with 3×30 ml of $CH_2Cl_2$. The combined extracts were dried ($K_2CO_3$) and evaporated in vacuo. The residue was dissolved in MeOH, neutralized with ethereal HCl followed by addition of ether to the cloud point giving crystals. Recrystallization from MeOH/ether and drying to constant weight in vacuo (20° C., 5 mm Hg) gave 8.47 g (74%) of pure N-(2,6-dimethoxyphenyl)-N'-(4,5,6,7-tetrahydro-1H-1,3-diazepin-2-yl)urea monohydrochloride; m.p. (180.5) 190°–192° C.; IR (CHCl$_3$) 3387, 1716, 1677, 1644 cm$^{-1}$. UV max. (MeOH) 243 nm ($\epsilon$=15,100).

ANAL. Calcd. for $C_{14}H_{20}N_4O_3 \cdot HCl$: C, 51.14; H, 6.44; N, 17.04, FOUND: C, 51.18; H, 6.45; N, 17.04.

EXAMPLE V

According to the teaching of Examples I–IV, the following compounds are prepared:

1. N-(2,6-Dimethylphenyl)-N'-(4,5,6,7-tetrahydro-1H-1,3-diazepin-2-yl)urea monohydrochloride; m.p. 164°–166° C. dec. 260°–263° C.

2. N-(2-Chloro-6-methylphenyl)-N'-(4,5,6,7-tetrahydro-1H-1,3-diazepin-2-yl)urea monohydrochloride; m.p. 159°–161° C. dec. 245°–250° C.
3. N-(2-Chloro-6-trifluoromethylphenyl)-N'-(4,5,6,7-tetrahydro-1H-1,3-diazepin-2-yl)urea monohydrochloride and acid addition salts (solvates).
4. N-(2,6-bis-Trifluoromethylphenyl)-N'-(4,5,6,7-tetrahydro-1H-1,3-diazepin-2-yl)urea monohydrochloride and acid addition salts (solvates).
5. N-(2-Methyl-6-trifluoromethylphenyl)-N'-(4,5,6,7-tetrahydro-1H-1,3-diazepin-2-yl)urea monohydrochloride and acid addition salts (solvates).
6. N-(2,6-Dibromophenyl)-N'-(4,5,6,7-tetrahydro-1H-1,3-diazepin-2-yl)urea monohydrochloride and acid addition salts (solvates).
7. N-(2,6-Difluorophenyl)-N'-(4,5,6,7-tetrahydro-1H-1,3-diazepin-2-yl)urea monohydrochloride and acid addition salts (solvates).
8. N-(2-Bromo-6-chlorophenyl)-N'-(4,5,6,7-tetrahydro-1H-1,3-diazepin-2-yl)urea monohydrochloride and acid addition salts (solvates).
9. N-(2-Chloro-6-fluorophenyl)-N'-(4,5,6,7-tetrahydro-1H-1,3-diazepin-2-yl)urea monohydrochloride and acid addition salts (solvates).
10. N-(2-Bromo-6-methylphenyl)-N'-(4,5,6,7-tetrahydro-1H-1,3-diazepin-2-yl)urea monohydrochloride and acid addition salts (solvates).
11. N-(2-Methoxy-6-trifluorophenyl)-N'-(4,5,6,7-tetrahydro-1H-1,3-diazepin-2-yl)urea monohydrochloride and acid addition salts (solvates).

EXAMPLE VI 1,000 hard gelatin capsules, each containing 200 milligrams of N-(2,6-dichlorophenyl)-N'-(4,5,6,7-tetrahydro-1H-1,3-diazepin-2-yl)urea are prepared from the following formulation:

|  | Grams |
|---|---|
| N—(2,6-Dichlorophenyl)-N'—(4,5,6,7-tetrahydro-1H—1,3-diazepin-2-yl)urea | 200 |
| Starch | 250 |
| Lactose | 750 |
| Talc | 250 |
| Calcium stearate | 10 |

A uniform mixture of the ingredients is prepared by blending and employed to fill two-piece hard gelatin capsules. The capsules are suitable to be orally administered to hypertensive subjects to reduce blood pressure.

EXAMPLE VII

Gelatin capsules are prepared as described in Example VI, except that in the formulation, 325 grams of N-(2,6-dimethylphenyl)-N'-(4,5,6,7-tetrahydro-1H-1,3-diazepin-2-yl)urea is employed as active agent providing capsules containing 325 milligrams of N-(2,6-dimethylphenyl)-N'-(4,5,6,7-tetrahydro-1H-1,3-diazepin-2-yl)urea.

EXAMPLE VIII 1,000 compressed tablets, each containing 500 milligrams of N-(2-chloro-6-methylphenyl)-N'-(4,5,6,7-tetrahydro-1H-1,3-diazepin-2-yl)urea are prepared from the following formulation.

|  | Grams |
|---|---|
| N—(2,6-dibromo-4-fluorophenyl)-N'—(4,5,6,7-tetrahydro-1H—1,3-diazepin-2-yl)urea | 500 |
| Starch | 750 |
| Dibasic calcium phosphate hydrous | 5,000 |
| Calcium stearate | 2.5 |

The finely powdered ingredients are mixed well and granulated with 10 percent starch paste. The granulation is dried and compressed into tablets using starch as a disintegrant and calcium stearate as a lubricant.

EXAMPLE IX

Tablets are prepared as described in Example VIII, except that N-(2,6-dibromophenyl)-N'-(4,5,6,7-tetrahydro-1H-1,3-diazepin-2-yl)urea is employed as active agent.

EXAMPLE X

Gelatin capsules are prepared as described in Example IX except that N-(2,6-dimethoxyphenyl)-N'-(4,5,6,7-tetrahydro-1H-1,3-diazepin-2-yl)urea is employed as active agent.

I claim:

1. A method of reducing arterial pressure in a hypertensive animal which comprises administering to said hypertensive animal, a therapeutically-effective antihypertensive amount of a compound selected from the group consisting of
   (a) an N-aryl-N'-(4,5,6,7-tetrahydro-1H-1,3,-diazepin-2-yl)urea having the formula:

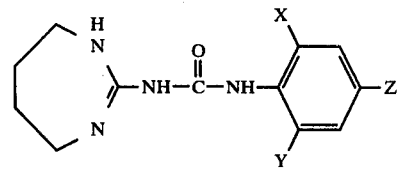

wherein X is Br, Cl, F, $CH_3$, $CF_3$ or $OCH_3$; Y is H, Br, Cl, F, $CH_3$, $CF_3$ or $OCH_3$; and Z is H or F; and
   (b) a pharmaceutically-acceptable salt thereof.

2. A method of reducing arterial pressure in hypertensive subjects which comprises administering to a hypertensive subject from about 1 to about 500 milligrams per unit dose of an N-aryl-N'-(4,5,6,7-tetrahydro-1H-1,3-diazepin-2-yl)urea compound represented by the formula:

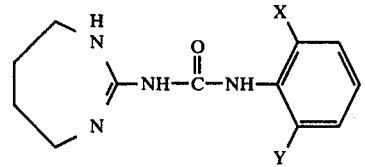

wherein X and Y are each independently selected from the group consisting of Br, Cl, $CH_3$ and $CF_3$; or a pharmaceutically-acceptable salt thereof.

3. A method according to claim 2 in which the urea compound is N-(2,6-dichlorophenyl)-N'-(4,5,6,7-tetrahydro-1H-1,3-diazepin-2-yl)urea, or a pharmaceutically-acceptable salt thereof.

4. A method according to claim 2 in which the urea compound is N-(2,6-dibromophenyl)-N'-(4,5,6,7-tetrahydro-1H-1,3-diazepin-2-yl)urea, or a pharmaceutically-acceptable salt thereof.

5. A method according to claim 2 in which the urea compound is N-(2,6-dimethylphenyl)-N'-(4,5,6,7-tetrahydro-1H-1,3-diazepin-2-yl)urea, or a pharmaceutically-acceptable salt thereof.

6. A method according to claim 2 in which the urea compound is N-(2-chloro-6-methylphenyl)-N'-(4,5,6,7-tetrahydro-1H-1,3-diazepin-2-yl)urea, or a pharmaceutically-acceptable salt thereof.

* * * * *